US009360404B2

(12) United States Patent
Okanojo et al.

(10) Patent No.: US 9,360,404 B2
(45) Date of Patent: Jun. 7, 2016

(54) FILTERING MEMBER AND FILTERING METHOD

(71) Applicant: Hitachi High-Technologies Corporation, Minato-ku, Tokyo (JP)

(72) Inventors: Masahiro Okanojo, Tokyo (JP); Hideyuki Noda, Tokyo (JP); Shinichi Fukuzono, Tokyo (JP); Kunio Harada, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/411,162

(22) PCT Filed: Jun. 7, 2013

(86) PCT No.: PCT/JP2013/065775
§ 371 (c)(1),
(2) Date: Dec. 24, 2014

(87) PCT Pub. No.: WO2014/002729
PCT Pub. Date: Jan. 3, 2014

(65) Prior Publication Data
US 2015/0192505 A1    Jul. 9, 2015

(30) Foreign Application Priority Data

Jun. 29, 2012 (JP) ................. 2012-146625

(51) Int. Cl.
*G01N 1/40* (2006.01)
*B01L 3/00* (2006.01)

(52) U.S. Cl.
CPC ............ *G01N 1/4077* (2013.01); *B01L 3/5635* (2013.01); *B01L 2300/0681* (2013.01); *B01L 2400/0487* (2013.01); *G01N 2001/4088* (2013.01)

(58) Field of Classification Search
CPC .... B01J 20/28033; B01J 20/30; B01D 61/36; B01D 61/38; G01N 33/491
USPC ................. 422/534–535, 513, 527, 547, 554; 436/177–178
See application file for complete search history.

(56) References Cited

U.S. PATENT DOCUMENTS 5,141,639 A    8/1992  Kraus et al.
5,156,811 A *  10/1992 White ............................ 422/513
(Continued)

FOREIGN PATENT DOCUMENTS

EP    1 541 668 A1    6/2005
EP    1 803 805 A1    7/2007
(Continued)

OTHER PUBLICATIONS

International Search Report (PCT/ISA/210) dated Aug. 27, 2013 with English translation (three pages).
(Continued)

*Primary Examiner* — Brian R Gordon
(74) *Attorney, Agent, or Firm* — Crowell & Moring LLP

(57) ABSTRACT

It has been difficult to conduct high-sensitivity, high-precision measurement due to externally generated contamination or cross-contamination. Thus, the invention includes (1) a filter unit having a filter at a bottom of a container for holding a liquid, the filter being adapted to filter a liquid, and (2) an attachment cover having a first opening and a second opening, the filter unit being attachable to and detachable from the attachment cover via the first opening, and the attachment cover being adapted to, when the filter unit is attached to the attachment cover, allow filtration by the filter in a state in which an inner face of the attachment cover is tightly in contact with an outer face of the filter unit, and discharge a resulting filtrate through the second opening.

5 Claims, 10 Drawing Sheets

(56) References Cited

U.S. PATENT DOCUMENTS

| | | | |
|---|---|---|---|
| 5,219,529 A * | 6/1993 | Ngo et al. | 422/527 |
| 5,556,598 A * | 9/1996 | Raybuck et al. | 422/525 |
| 6,117,394 A * | 9/2000 | Smith | 422/513 |
| 6,319,236 B1 | 11/2001 | Boeck | |
| 8,414,778 B2 * | 4/2013 | Tajima et al. | 210/744 |
| 2009/0294385 A1 | 12/2009 | Tajima et al. | |

FOREIGN PATENT DOCUMENTS

| | | |
|---|---|---|
| EP | 1 873 231 A1 | 1/2008 |
| JP | 6-315603 A | 11/1994 |
| JP | 3527153 B2 | 5/2004 |
| JP | 2004-317179 A | 11/2004 |
| JP | 2005-291940 A | 10/2005 |
| WO | WO 98/20352 A2 | 5/1998 |
| WO | WO 2006/123688 A1 | 11/2006 |

OTHER PUBLICATIONS

Japanese-language Written Opinion (PCT/ISA/237) dated Aug. 27, 2013 (four pages).

Hattori et al. "Enhanced microbial biomass assay using mutant luciferase resistant to benzalkonium chloride" Analytical Biochemistry, Science Direct, 2003, pp. 287-295, vol. 319, Academic Press.

Japanese Office Action issued in counterpart Japanese Application No. 2012-146625 dated Jan. 12, 2016 (five (5) pages).

Extended European Search Report issued in counterpart European Application No. 13809758.9 dated Feb. 2, 2016 (Nine (9) pages).

* cited by examiner

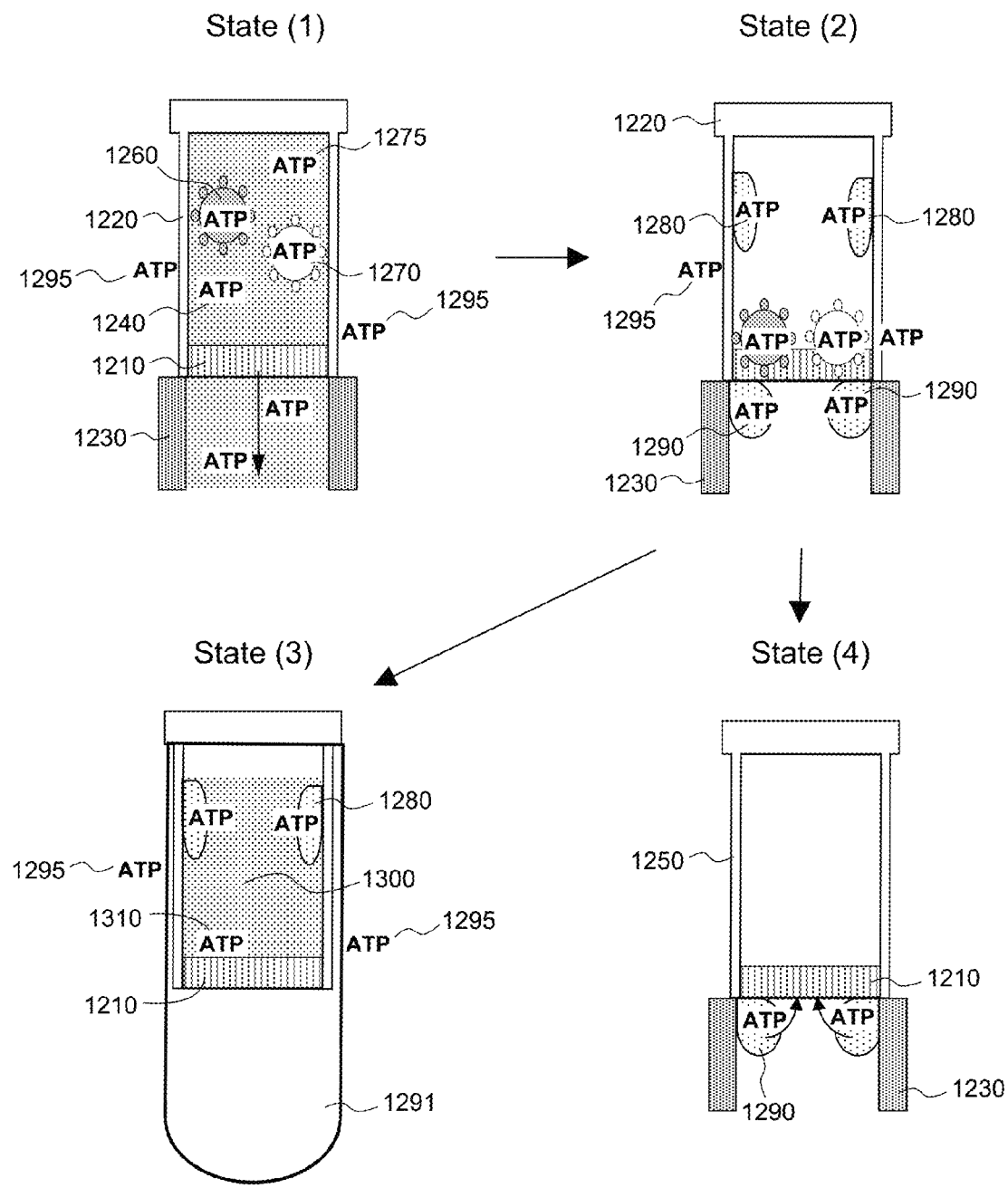

)# FILTERING MEMBER AND FILTERING METHOD

TECHNICAL FIELD

The present invention relates to a filtering member for use in filtering a sample containing cells, and a filtering method that uses such a member.

BACKGROUND ART

In recent years, a method for evaluating the state of cells by conducting analysis on a per-cell basis has been drawing attention. Such a method is called single cell analysis, which is one of the important analytical methods conducted in sterile tests during manufacture of pharmaceuticals and in regenerative medicine typified by iPS (induced pluripotent stem) cells.

A measurement method that physically, chemically, or biologically analyzes an extremely small number of cells in a sample typically requires high sensitivity and precision. Therefore, for such type of measurement, a method for condensing cells, which are the measurement targets, using a filter by filtering a sample under a sterile environment and thus removing unnecessary mediums is used. There are also cases in which a filter with an analytical reagent added thereto is heated or cooled as needed in order to activate or inactivate reactions of the analytical reagent, or a filter is moved to an analyzer or the like.

In sterile tests, members that are used for filtering a sample, causing a reaction of a reagent, and moving an analyte should be in sterile conditions. Further, in sterile tests, it is required that not only a sample be easy to handle, but also contamination from a variety of contamination sources (e.g., an operator, measurement environment, or unnecessary samples remaining after filtration) be prevented. Furthermore, it is extremely important to prevent mutual contamination between samples, that is, cross-contamination in order to analyze a small number of valuable cells with high sensitivity and high-precision.

Hereinafter, the background art of a method for measuring bacterial cells using a bioluminescence method will be described. In the pharmaceutical manufacturing field, the cosmetic manufacturing field, the clinical medicine field, the basic biochemical field, and the like, determination of whether or not a sample contains bacterial cells and measurement of the number of bacterial cells are widely conducted in order to control quality of sample. For example, in the pharmaceutical manufacturing field, it is essential to manage bacterial cells (microbes or funguses) contained in the raw materials, intermediates, and end products of pharmaceuticals, or in pharmaceutical manufacturing water based on the Japanese pharmacopoeia standardized by the Japanese Ministry of Health, Labour and Welfare. Thus, the number of bacterial cells is measured each day.

The main method for measuring the number of microbes or funguses, which is standardized by the Japanese pharmacopoeia, is the culture method.

TABLE 1

|  | Bioluminescence Method | Fluorescent Staining Method | Culture Method |
| --- | --- | --- | --- |
| Detection Targets | ATP Molecules Extracted from Cells | Cells containing DNA | Cells |

TABLE 1-continued

|  | Bioluminescence Method | Fluorescent Staining Method | Culture Method |
| --- | --- | --- | --- |
| Detection Method | Luminescent Reaction of ATP-Luciferase | Fluorescence Reaction between DNA and Fluorescent Dye | Visual Observation of Colony |
| Do Detection Targets Pass through Filter? | Pass | Not Pass | Not Pass |

In the culture method, a sample is first filtered through a filter to trap bacterial cells, and then, the filter that has trapped the bacterial cells is put on an agar plate for cultivation. At this time, a single bacterial cell forms a single colony. As the culture method, the number of colonies (CFU: colony forming unit) that can be measured is counted through visual observation using such characteristics, thereby quantitatively determining the count of viable bacteria in the sample. It should be noted that dead bacteria will not grow even when they are cultured, and will not form colonies. Thus, such bacteria are not visually observed.

By the way, in the pharmaceutical industry, bacterial cells under an oligotrophic environment, such as in pharmaceutical manufacturing water, are the detection targets. Therefore, a time as long as about one week is needed to culture such bacterial cells, which is problematic in detection. This, in turn, can take a long time to prepare test results in the stage of manufacturing intermediates or shipping final products. Thus, the culture method burdens the business operators both temporally and economically.

Meanwhile, the fluorescent staining method is known as a method that can rapidly measure bacterial cells. Patent Literature 1 describes an example of a microorganism collecting kit used in the fluorescent staining method. The microorganism collecting kit described in Patent Literature 1 is used by combining a filter for removing foreign matter as a pre-filter with a filter for collecting microorganisms, and is characterized in that the base main body of the filter is reusable.

In the latest fluorescent staining method, a sample containing bacterial cells is filtered first, and then, DNA (deoxyribonucleic acid) in the bacterial cells is stained using a fluorescent dye. There is known a method that uses two types of dyes: a fluorescent dye for concurrently staining DNA in viable bacteria and DNA in dead bacteria, and a fluorescent dye for staining only DNA in dead bacteria. Such a method can separately measure viable bacteria and dead bacteria.

However, in the fluorescent staining method, fine particles, dust, and the like other than bacterial cells would be concurrently detected if they emit fluorescence with the same wavelength as the fluorescent dye. Thus, the fluorescent staining method has a problem in that the reliability of the detection results of bacterial cells is unstable.

Besides, the ATP (adenosine triphosphate) bioluminescence method is known as a method for rapidly measuring bacterial cells using a principle other than fluorescence measurement. ATP molecules, which are the detection targets of this method, are organic compounds that exist in cells of all living organisms, and are the sources of energy that is necessary for vital activities of the cells. In the bioluminescence method, luciferase and luciferin that emit light upon chemically reacting with ATP are used, so that luminescence generated by a luminescent reaction between ATP extracted from cells and luciferase or luciferin is measured to estimate the number of cells from the amount of luminescence.

In the conventional method, a sample containing ATP derived from viable bacteria and dead bacteria as well as ATP in the free state is subjected to the following three stages: (1) removal of ATP other than ATP derived from viable bacteria, (2) extraction of ATP in the viable bacteria, and (3) a luminescent reaction between ATP derived from the viable bacteria and a luminous reagent (e.g., luciferase and luciferin) and measurement of the luminescence.

The amount of ATP contained in each viable bacterium is as small as about $1.5 \times 10^{-18}$ mol/CFU (0.001 fmol/CFU=1 amol/CFU) when calculated in terms of 1 CFU of bacterium (Non Patent Literature 1). The ATP detection sensitivity of the currently available common bioluminescence method is $1 \times 10^{-15}$ to $1 \times 10^{-16}$ mol (1 to 0.1 fmol).

CITATION LIST

Patent Literature

Patent Literature 1: JP 2005-291940 A
Patent Literature 2: JP 3527153 B
Patent Literature 3: U.S. Pat. No. 5,141,639 A Non Patent Literature Non Patent Literature 1: Analytical Biochemistry, Volume 319, pp. 287 to 295, 2003

SUMMARY OF INVENTION

Technical Problem

The inventors of the present application are now developing an ATP measurement technique with ultrahigh sensitivity at a level as high as $1.0 \times 10^{-18}$ mol that cannot be easily achieved at present. During the development, the inventors have found that contamination by ATP at a quite low level, which is usually inconceivable, can occur. The inventors have also found that it would be impossible to obtain reliable measurement results at a level of $1.0 \times 10^{-18}$ mol unless such contamination problem is solved. That is, the inventors have found that it is necessary to achieve a measurement environment in which contamination by even 1 atom ATP is not allowed in order to obtain measurement results at the target level.

In the conventional rapid measurement of bacterial cells, an operator, when filtering a sample containing bacterial cells, directly grips a filter or a container with a filter fixed thereon with tweezers or fingers, and connects and sets the filter or the container to/at a filter port. After that, the operator starts filtration by directly pouring a sample onto the filter or by connecting a container filled with a sample to the container with the filter fixed thereon. After the filtration, the operator adds a reagent onto the filter as needed, and sets the filter or the member with the filter fixed thereon in a thermostatic device while directly gripping the filter or the member with the filter fixed thereon in order to promote reactions of the reagent or promote growth of the trapped bacterial cells. After that, the filter is washed as needed to remove the reagent, and the bacterial cells trapped by the filter are analyzed physically, chemically, or biologically. At this time, the operator moves the filter or the member with the filter fixed thereon to an analyzer or the like by directly gripping the filter or the member with the filter fixed thereon.

In the aforementioned plurality of operations in which the filter or the container with the filter fixed thereon should be contacted, there may be cases where the non-contaminated state of the filter or the container with the filter fixed thereon is lost due to contamination from the operator or the measurement environment.

Solution to Problem

The present specification includes a plurality of means for solving the aforementioned problem, and some of them include a "filtering member" and a "filtering method" described below.

For example, one of the means is a "filtering member including (1) a filter unit having a filter at a bottom of a container for holding a liquid, the filter being adapted to filter a liquid; and (2) an attachment cover having a first opening and a second opening, the filter unit being attachable to and detachable from the attachment cover via the first opening, and the attachment cover being adapted to, when the filter unit is attached to the attachment cover, allow filtration by the filter in a state in which an inner face of the attachment cover is tightly in contact with an outer face of the filter unit, and discharge a resulting filtrate through the second opening."

Another means is a "filtering member including (1) a filter unit having a filter at a bottom of a container for holding a liquid, the filter being adapted to filter a liquid; (2) an attachment cover having a first opening and a second opening, the filter unit being attachable to and detachable from the attachment cover via the first opening, and the attachment cover being adapted to, when the filter unit is attached to the attachment cover, allow filtration by the filter in a state in which an inner face of the attachment cover is tightly in contact with an outer face of the filter unit, and discharge a resulting filtrate through the second opening; and (3) an inner attachment having a first opening and a second opening, the inner attachment on the first opening side being attachable to and detachable from an inside of the filter unit, and the inner attachment being adapted to, when attached to the filter unit, be in contact with the filter unit such that an outer face of the inner attachment is tightly in contact with an inner face of the filter unit."

Further another means is a "filtering method including a step of controlling a process of filtering a sample using a filtering member having mounted thereon (1) a filter unit, (2) an attachment cover, and (3) an inner attachment, the (1) filter unit having a filter at a bottom of a container for holding a liquid, the filter being adapted to filter a liquid, the (2) attachment cover having a first opening and a second opening, the filter unit being attachable to and detachable from the attachment cover via the first opening, and the attachment cover being adapted to, when the filter unit is attached to the attachment cover, allow filtration by the filter in a state in which an inner face of the attachment cover is tightly in contact with an outer face of the filter unit, and discharge a resulting filtrate through the second opening, and the (3) inner attachment having a first opening and a second opening, the inner attachment on the first opening side being attachable to and detachable from an inside of the filter unit, and the inner attachment being adapted to, when attached to the filter unit, be in contact with the filter unit such that an outer face of the inner attachment is tightly in contact with an inner face of the filter unit; a step of controlling an arm with a control unit to detach the inner attachment from the filter unit; a step of controlling, with the control unit, addition of a reaction solution into the filter unit from which the inner attachment has been detached, thereby causing at least one reaction to occur between a sample trapped by the filter and the reaction solution; a step of controlling the arm with the control unit to detach the attachment cover from the filter unit; and a step of causing, with the control unit, a reaction to occur between a reactant of the sample and a newly added reaction solution in the filter unit."

Advantageous Effects of Invention

According to the present invention, it is possible to, in conducting measurement with a bioluminescence method, avoid influence of externally generated contamination on measurement results and thus analyze samples with high sensitivity and high precision. Other problems, structures, and advantageous effects will become apparent from the following description of embodiments.

BRIEF DESCRIPTION OF DRAWINGS

FIG. 6A illustrates a cause of contamination of a filter unit by ATP (conventional structure).

DESCRIPTION OF EMBODIMENTS

Hereinafter, embodiments of the present invention will be described with reference to the drawings. It should be noted that the embodiments of the present invention are not limited to those described below, and a variety of variations are possible within the spirit and scope of the invention.
[Embodiment]

First, a filtering member in accordance with this embodiment will be described. A filtering member described below is structurally characterized by providing high operability in addition to preventing contamination from an operator or a measurement environment, preventing generation of residues of samples (avoiding cross-contamination), and preventing generation of air locks during filtering. Such characteristics allow implementation of high-sensitivity, high-precision analysis with a bioluminescence method.
[Structure of Components of Filtering Member]

Figure 1A:
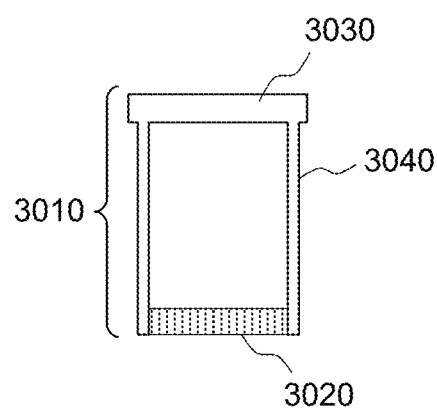
FIG. 1A shows an exemplary cross-sectional structure of a filter unit (Embodiment).

FIG. 1A shows an exemplary structure of a filter unit 3010. The filter unit 3010 has a structure in which a filter 3020 is fixed on one of the openings of a cylindrical housing 3040, for example. The filter 3020 can filter a liquid. The filter 3020 forms the bottom of the housing 3040, and can hold a liquid within an inner space surrounded by the housing 3040 and the filter 3020. The other opening of the housing 3040 is used as a sample inlet 3030. As described below, an inner attachment 3500 is mounted from the sample inlet 3030 in the direction of the filter 3020. It should be noted that the housing 3040 around the sample inlet 3030 has formed thereon a flange portion that protrudes outward from the side face. The flange portion is used as a stopper for mounting the inner attachment 3500 on the filter unit 3010.

Figure 1B:
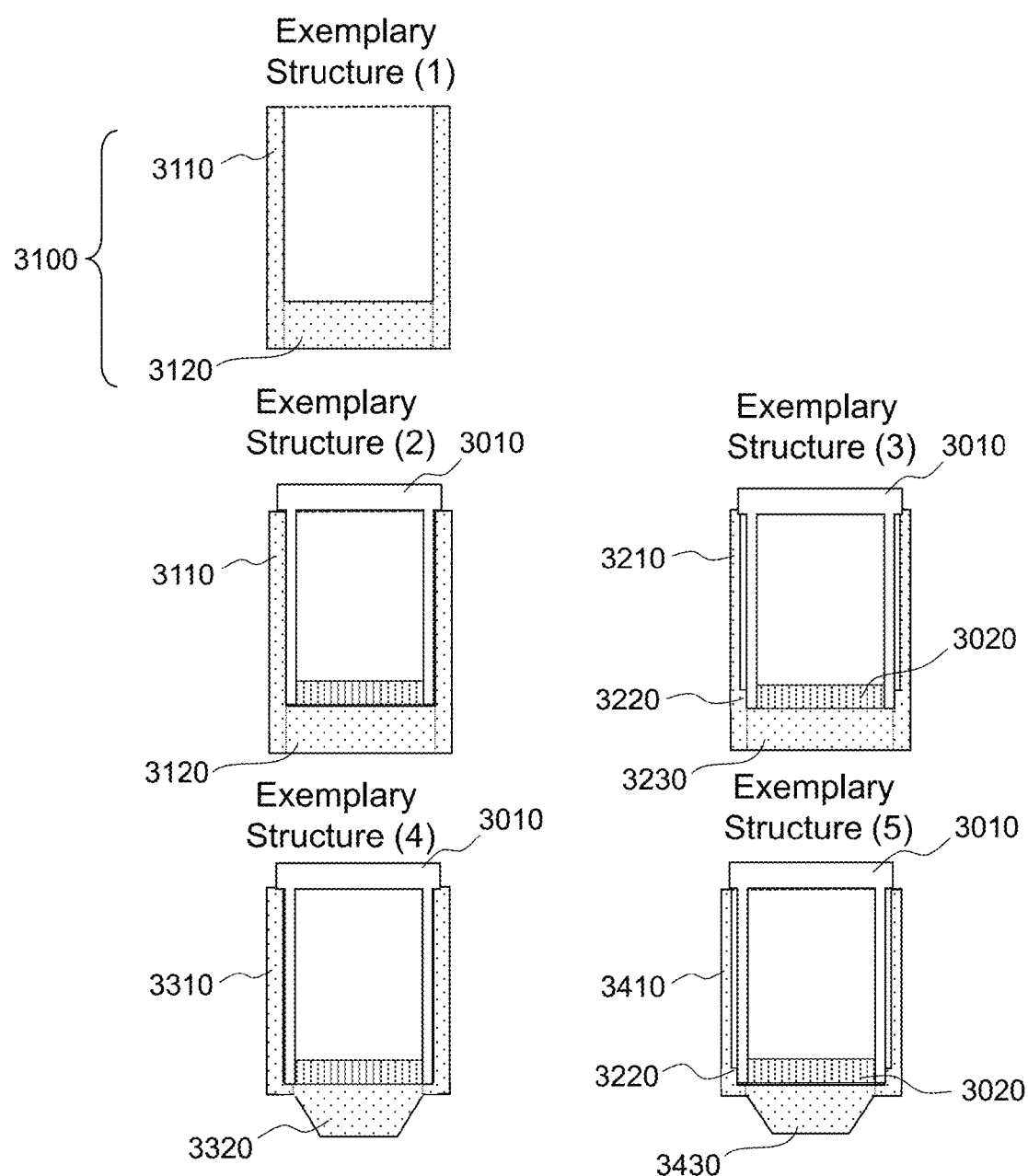
FIG. 1B shows exemplary cross-sectional structures and exemplary mounting of an attachment cover (Embodiment).

FIG. 1B shows exemplary structures and exemplary mounting of an attachment cover 3100 in which the filter unit 3010 is detachably mounted. As shown in an exemplary structure (1), the attachment cover 3100 has a cylindrical housing 3110 as a basic structure. In this specification, one of the openings of the cylinder will be referred to as a first opening and the other opening will be referred to as a second opening.

The filter unit 3010 can be detachably mounted on the attachment cover 3100 from the side of the first opening. The attachment cover 3100 functions as a cover that covers the side face and the bottom of the filter unit 3010. That is, the operator directly touches only the attachment cover 3100, and thus is able to avoid touching the filter 3020 and the filter unit 3010. Thus, unlike with the conventional structure, contamination of the filter 3020 and the filter unit 3010 by the operator can be prevented.

The attachment cover 3100 has an inner side face (i.e., hermetically sealed portion) on which the filter unit 3010 can be mounted with airtightness maintained between the inner side face of the attachment cover 3100 and the outer side face of the filter unit 3010. Therefore, the inner diameter of the attachment cover 3100 is formed slightly larger than the outer diameter of the filter unit 3010.

In addition, a filtrate passage 3120 that, when the filter unit 3010 is mounted, extends in the direction of the attachment plane of the filter 3020 is formed around the second opening of the attachment cover 3100. With the presence of the filtrate passage 3120, it is possible to filter a sample in a state in which the filter unit 3010 is attached to the attachment cover 3100. The resulting filtrate passes through the filtrate passage 3120, and is then discharged from the second opening.

With the above structure, it is possible to, even when the surface of the attachment cover 3100 is externally contaminated or a filtrate remains in the filtrate passage 3120, prevent a circumstance in which the filter 3020 is contaminated by the filtrate that remains on the attachment cover 3100 or in the filtrate passage 3120, by detaching the attachment cover 3100 from the filter unit 3010.

It should be noted that the tightly attached portion between the attachment cover 3100 and the filter unit 3010 is desirably provided at a portion around the filter 3020 that is fixed on the filter unit 3010 and a portion around the bottom of the filter.

The attachment cover 3100 can be connected to a filter port, which is described below, on the second opening side, and is detachable from the filter port after filtration. Even when a filtrate remains in the filter port after filtration, a new attachment cover 3100 will be interposed between the filter 3020 and the remaining filtrate. Thus, there is no possibility that the new filter 3020 attached to the new attachment cover 3100 will be contaminated by the residue of the filtrate.

In order to reduce the possibility of contamination of a portion around the filter port by a filtrate, the shape of the filtrate passage of the attachment cover 3100 on the second opening side is desirably a tapered shape that allows the filtrate passage to be inserted into the filter port.

Hereinafter, the state in which the attachment cover 3100 is tightly attached to the filter unit 3010, and other exemplary structures of the attachment cover 3100 will be described with reference to exemplary structures (2) to (5). The attachment cover 3100 shown in the exemplary structure (2) has a structure in which the cover is tightly attached almost on the entire inner side face of the housing 3110. The filtrate passage 3120 is arranged such that it is opposite the filter 3020. The attachment cover 3100 shown in an exemplary structure (2) has a simple structure. Thus, the attachment cover 3100 shown in the exemplary structure (2) is advantageous for reducing cost in the mass production.

The attachment cover 3100 shown in an exemplary structure (3) has an upper stage face and a lower stage face on the inner side face of a housing 3210, and has a structure in which the attachment cover 3100 is tightly attached to the filter unit 3010 on the upper stage face that is provided around the outer circumferential face of the filter 3020. That is, shown herein is an example in which a tightly attached portion 3220 is formed around the outer circumferential face of the filter 3020.

In the exemplary structure (3), the area of the attachment cover 3100 that is tightly attached to the filter unit 3010 can be smaller than that of the exemplary structure (2). Therefore, it is possible to easily detach the filter unit 3010 from the attachment cover 3100. In addition, in the exemplary structure (3), the filter 3020 can be efficiently heated and cooled via the housing 3210 and the tightly attached portion 3220. In such an exemplary structure, a filtrate passage 3230 is also formed at a position opposite the filter 3020.

The attachment cover 3100 shown in the exemplary structure (4) is a variation of the attachment cover 3100 shown in the exemplary structure (2). A housing 3310 of the attachment cover 3100 shown in the exemplary structure (4) has a filtrate passage 3320 that is formed in a taper shape. As the filtrate passage 3320 is tapered, the filtrate passage 3320 can be easily inserted into the filter port. Further, as the sloped face of the filtrate passage 3320 is inclined in the direction of the center axis, a filtrate flows out in the direction of the center axis. That is, the scattering range of a filtrate is difficult to expand than the diameter of the outlet. Therefore, contamination of the a portion around the filter port by the filtrate can be minimized.

The attachment cover 3100 shown in the exemplary structure (5) is a variation of the attachment cover 3100 shown in the exemplary structure (3). The exemplary structure (5) differs from the exemplary structure (3) in that a housing 3410 of the attachment cover 3100 shown in the exemplary structure (5) has a filtrate passage 3430 that is formed in a taper shape. Such a shape allows the filter unit 3010 to be easily detached from the attachment cover 3100, and allows efficient heating and cooling of the filter 3020 via the housing 3410 and the tightly attached portion 3220. Further, as the filtrate passage 3430 can be more easily inserted into the filter port, contamination of a portion around the filter port by a filtrate can be minimized.

Figure 1C:
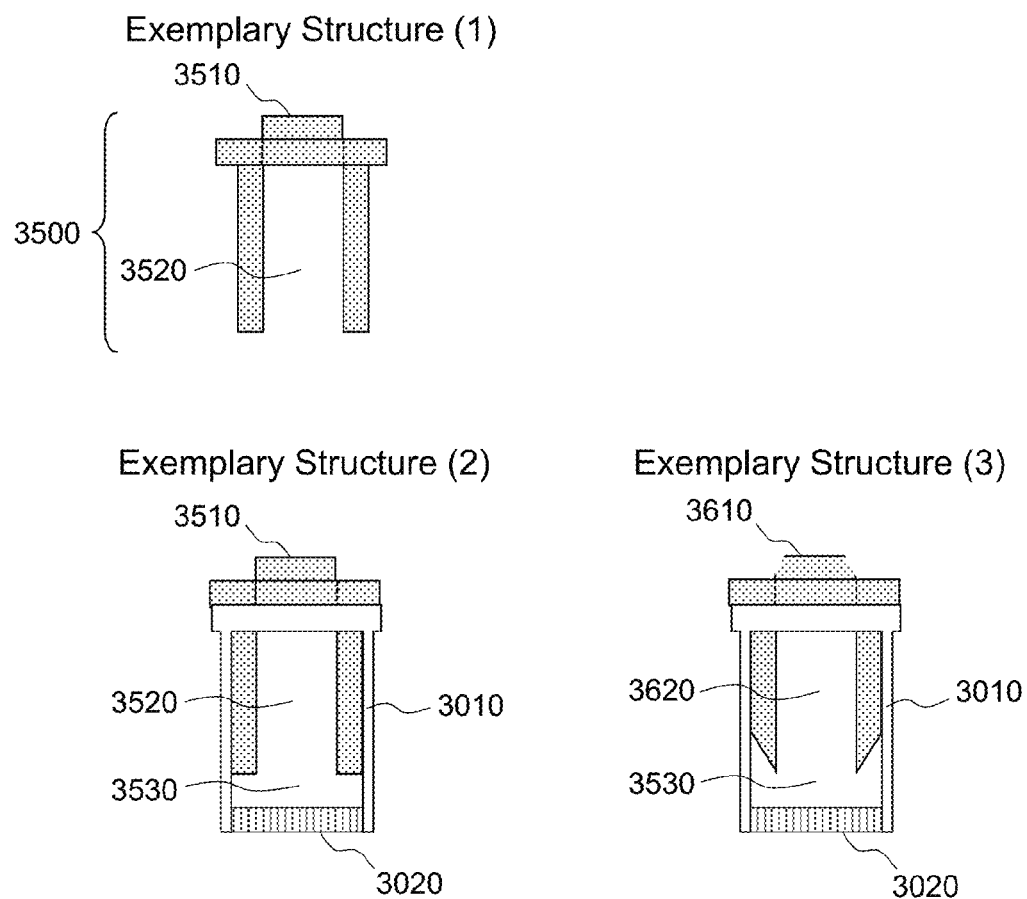
FIG. 1C shows exemplary cross-sectional structures and exemplary mounting of an inner attachment (Embodiment).

FIG. 1C shows exemplary structures and exemplary mounting of the inner attachment 3500 that is detachably mounted on the inner side of the filter unit 3010.

The inner attachment 3500 has a cylindrical housing 3505 as a basic structure as shown in an exemplary structure (1). In this specification, one of the openings of the cylinder will be referred to as a first opening, and the other opening will be referred to as a second opening.

In FIG. 1C, a portion of the housing that is inserted into the filter unit 3010 corresponds to the first opening, and such portion of the housing will be referred to as a sample passage 3520. Meanwhile, a portion of the housing that covers the upper face of the filter unit 3010 when the inner attachment 3500 is attached to the filter unit 3010 corresponds to the second opening. Such portion of the housing will be referred to as a sample inlet 3510 in this specification.

The outer circumferential face of the sample passage 3520 is processed in a shape that can maintain air tightness between the outer circumferential face of the sample passage 3520 and the inner side face of the filter unit 3010 when mounted. That is, the diameter of the outer circumferential face of the sample passage 3520 is formed slightly smaller than the diameter of the inner circumferential face of the filter unit 3010. The sample passage 3520 functions as a cover for the inner side face of the filter unit 3010 when mounted.

As described above, as the inner side face of the filter unit 3010 is covered with the sample passage 3520, it is possible to prevent a sample from remaining on the inner side face of the filter unit 3010 after termination of the measurement. In addition, even when a sample remains on the inner side of the inner attachment 3500, it is possible to prevent contamination of the filter 3010 by the remaining sample only by detaching the inner attachment 3500.

Meanwhile, the sample inlet 3510 has formed therein a through-hole (not shown) for allowing a sample to be introduced into the inside from the outside. Covering the upper face of the filter unit 3010 with the sample inlet 3510 can prevent contamination of the filter unit 3010 by the operator or the measurement environment.

Hereinafter, the state in which the inner attachment 3500 is tightly attached to the filter unit 3010 and another exemplary structure of the inner attachment 3500 will be described with reference to exemplary structures (2) to (3).

The inner attachment 3500 shown in the exemplary structure (2) is the same as that of the exemplary structure (1). There is no possibility that the tip end of the sample passage 3520 will contact the filter 3020 in the state in which the inner attachment 3500 is attached to the filter unit 3010. In this specification, a clearance portion formed between the tip end of the sample passage 3520 and the filter 3020 will be referred to as a noncontact portion 3530. The noncontact portion 3530 forms an escape route for air bubbles that would otherwise be mixed when a sample is introduced into the filter unit 3010. With the presence of the noncontact portion 3530, it is possible to avoid generation of air locks, thereby preventing the filtration area of the filter 3020 from being lost. Further, providing the noncontact portion 3530 can prevent adsorption of a sample onto the inner circumferential face of the filter unit 3010.

The inner attachment 3500 shown in the exemplary structure (3) has a sample passage 3620 with a tip end processed in a tapered shape. In the drawing, the sample passage 3620 on the outer side face side is processed in a taper shape so that a space is formed between the outer side face of the sample passage 3620 and the inner side face of the filter unit 3010. In the exemplary structure (3), the noncontact portion 3530 is also formed between the tip end of the sample passage 3620 and the filter 3020 as in the exemplary structure (2). Therefore, even when air bubbles are mixed into a sample, it is possible to ensure an escape route for the air, thereby preventing the filtration area of the filter 3020 from being lost. In addition, providing the noncontact portion 3530 can more easily prevent adsorption of a sample onto the inner circumferential face of the filter unit 3010.

A sample inlet 3610 of the inner attachment 3500 is processed such that the diameter of its flow passage expands in the direction of the sample passage 3620 from the side of the opening though which a sample is introduced. That is, the sample inlet 3610 is processed in a taper shape. As the sample inlet 3610 is processed in a taper shape, it is possible to, when a sample introduced, reduce the resistance between the sample and the inner wall of the flow passage. Consequently, turbulence will become less likely to be generated when a sample is introduced, and thus, mixture of air bubbles can be effectively prevented.

[Use Example of Filtering Member]

Figure 1D:
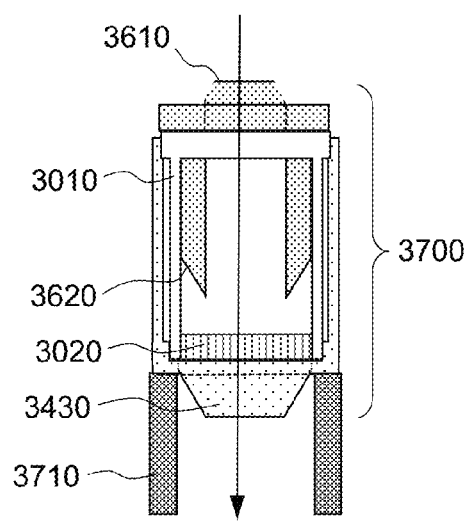
FIG. 1D shows the assembled state of a filtering member and a use example thereof (Embodiment).

FIG. 1D shows the state in which a filtering member 3700 assembled from the filter unit 3010, the attachment cover 3100, and the inner attachment 3500 is arranged at a filter port 3710. It should be noted that FIG. 1D represents a case where the filter unit 3010 shown in FIG. 1A, the attachment cover 3100 shown in the exemplary structure (5) of FIG. 1B, and the inner attachment 3500 shown in the exemplary structure (3) of FIG. 1C are assembled. As shown in FIG. 1D, the filtrate passage 3430 is tapered. Thus, the filtrate passage 3430 can be attached such that it is inserted into the filter port 3710.

A sample is introduced from the sample inlet 3610 of the inner attachment 3500 as shown in the arrow in FIG. 1D, and then, the sample passes through the sample passage 3620 and reaches the filter 3020 of the filter unit 3010. Herein, the sample is filtered by the filter 3020, and then, the filtrate passes through the filtrate passage 3430 of the attachment cover 3100 and is discharged to the inside of the filter port 3710. At this time, it is desirable that the degree of adhesion A1 between the inner attachment 3500 and the filter unit 3010 and the degree of adhesion A2 between the attachment cover 3100 and the filter unit 3010 satisfy a relationship of A2>A1.

Upon termination of the sample filtration, the operator detaches the inner attachment 3500 from the filter unit 3010. By such operation, a sample that has remained on the inner side face of the inner attachment 3500 is removed together with the inner attachment 3500.

Next, the operator adds a reagent into the filter unit 3010. After that, the operator detaches the attachment cover 3100 on which a filtrate remains from the filter unit 3010. When the degree of adhesion satisfies the aforementioned relationship, the components can be easily detached in sequence. Accordingly, contamination of the filter 3020 and the filter unit 3010 can be prevented.

Figure 2:
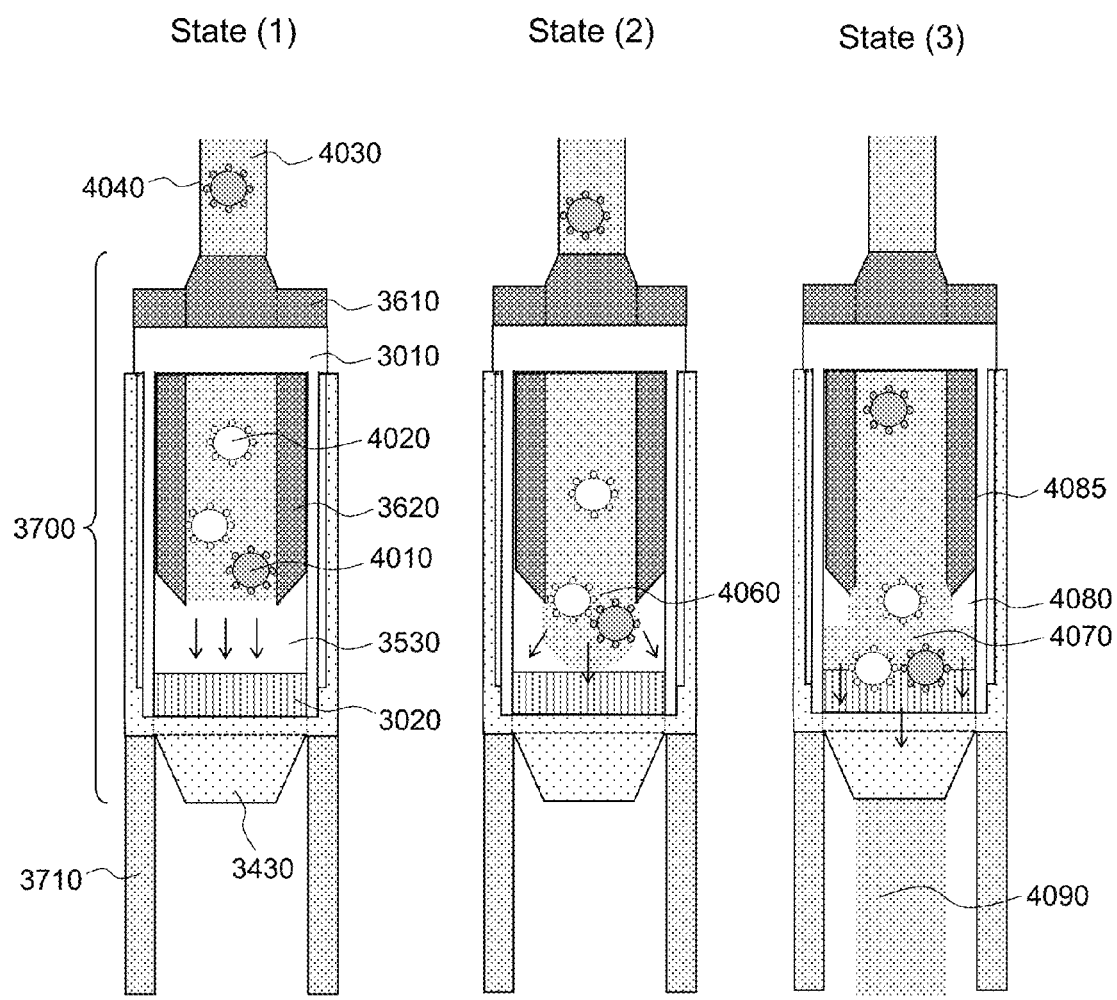
FIG. 2 illustrates a filtering step with a filtering member (Embodiment).

FIG. 2 shows the details of the operation of filtering a sample 4030 using the filtering member 3700 in accordance with this embodiment. It should be noted that the sample 4030 contains viable bacteria 4010 and dead bacteria 4020.

A state (1) represents the state in which the filtering member 3700 is set at the filter port 3710 when filtration is started. In the drawing, a tube 4040 is attached to the sample inlet 3610 of the inner attachment 3500 to supply the sample 4030 from a sample container (not shown). In addition, the filtrate passage 3430 that has been processed in a taper shape is attached such that it is inserted into the filter port 3710.

A flow passage in the connection portion between the tube 4040 and the sample inlet 3610 is processed in a taper shape. Therefore, it is possible to prevent generation of turbulence in the flow of the sample 4030 at the sample inlet 3610 and thus avoid mixture of air bubbles into the sample 4030.

At this stage, when a pressure difference (e.g., negative pressure) is generated between the filter 3020 and the filter port 3710, the sample 4030 is introduced into the inside of the filtering member 3700 via the tube 4040 and the sample inlet 3610. The state (1) represents the state in which the inside of the inner attachment 3500 is filled with the sample 4030.

Eventually, the state transitions to a state (2). As shown in the drawing, the noncontact portion 3530 is provided between the opening of the sample passage 3620 of the inner attachment 3500 and the filter 3020. In addition, as shown in the drawing, the inner diameter of the filter unit 3010 is larger than the diameter of the opening of the sample passage 3620. Thus, the sample 4030 grows such that a droplet 4060 with a larger diameter than the diameter of the opening forms. The length of the noncontact portion 3530 in the height direction is desirably greater than or equal to the diameter of the droplet. Eventually, the sample 4030 reaches the surface of the filter 3020 in the state of the droplet 4060. It should be noted that the length of the noncontact portion 3530 in the height direction is desirably less than or equal to double the diameter of the droplet.

When the droplet 4060 falls onto the surface of the filter 3020, the state transitions to a state (3). When the droplet 4060 sticks to the surface of the filter 3020, the droplet 4060 temporarily resides on the surface of the filter 3020 due to resistance that is produced by the thin pores formed in the filter 3020. Accordingly, the droplet 4060 turns into a state 4070 of temporarily residing on the surface of the filter 3020. After that, the droplet 4060 is filtered through the pores of the filter 3020.

With the movement of the droplet 4060, a space 4080 is formed between the droplet 4060 and the inner wall of the filter unit 3010. With the presence of such space 4080, it is possible to, even when air bubbles are generated in the sample, allow the air bubbles to escape into the space 4080, and thus prevent generation of air locks due to the air.

The droplet 4060 that has fallen onto the filter 3020 expands along the surface of the filter 3020, and turns into the state 4070 of temporarily residing on the surface of the filter 3020. Therefore, there is no possibility that the sample 4030 may scatter to the inner wall of the filter unit 3010. Accordingly, it is possible to prevent inflow of the sample 4030 into a clearance 4085, which is formed between the inner attachment 3500 serving as the outer side face and the filter unit 3010 serving as the inner side face, which would otherwise occur due to the capillary action.

The viable bacteria 4010 and the dead bacteria 4020 contained in the sample 4030 are trapped depending on the size of the pores. The sample 4030 that has been filtered through the filter 3020 and reached the filtrate passage 3430 is directly discharged as a filtrate 4090 into the filter port 3710.

Exemplary Sample Introduction Method

Figure 3:
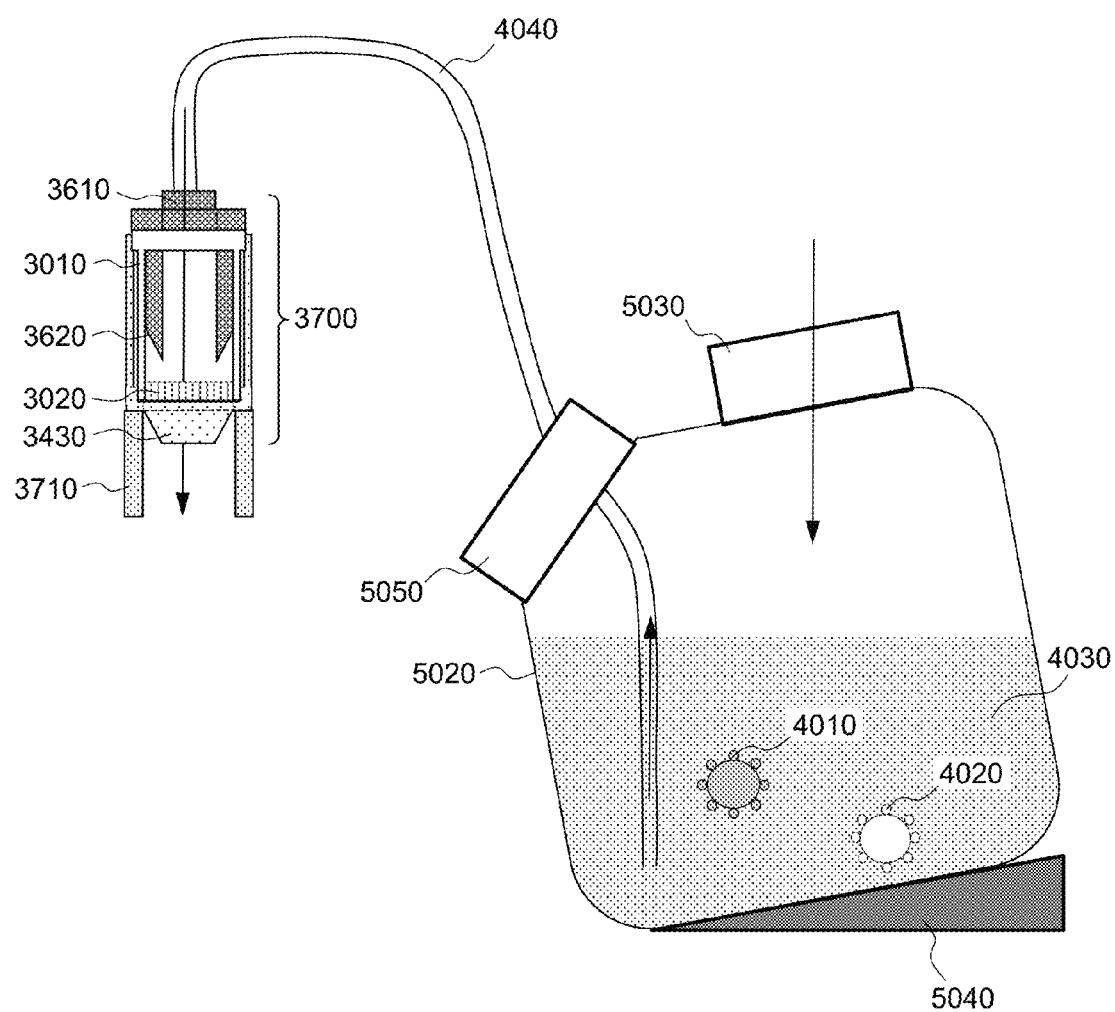
FIG. 3 illustrates a step of filtering a large amount of sample using a filtering member (Embodiment).

FIG. 3 shows an embodiment of a sample introduction method. It is assumed that an operator carries the filtering member 3700, the tube 4040, and a sample container 5020 as appropriate. At this time, the operator will touch such members, but will not directly touch the filter 3020 or the filter unit 3010. This is because the surfaces of the filter 3020 and the filter unit 3010 are covered with the attachment cover 3100 and the inner attachment 3500 as described above. Accordingly, there is no possibility that the filter 3020 and the filter unit 3010 will be contaminated by the operator or the measurement environment.

For example, the operator opens a sample inlet cap 5030 at any place, and introduces the sample 4030, which may possibly contain viable bacteria 4010 and dead bacteria 4020, into the sample container 5020. In order to surely filter the sample 4030, a tilt table 5040 may be used. The tube 4040 is connected to the sample inlet 3610 of the inner attachment 3500 via a sample outlet cap 5050 of the sample container 5020.

As described previously, a pressure difference is generated between the filter port 3710 and the filter 3020, whereby the sample 4030 flows through the tube 4040 and reaches the filter 3020 through the sample inlet 3610 to the sample passage 3620 of the inner attachment 3500. Then, the sample 4030 is filtered through the filter 3020. Consequently, bacterial cells are trapped by the filter 3020. The resulting filtrate passes through the filtrate passage 3430 of the attachment cover 3500, and is then discharged to the inside of the filter port 3710.

With such a method, the operator is able to have any amount of the sample 4030 filtered independently of the shape of the filtering member 3700, by preparing a preferred sample container 5020. The sample container 5020, which is connected to the filtering member 3700 via the tube 4040, may be a beaker, an Erlenmeyer flask, a plastic bottle, or the like. It is also possible to join the sample inlet port 3510 of the inner attachment 3500 to a needle of a syringe if necessary. Even in such a case, filtration of the sample 4030 is possible.

[Operations and Process Flow of Sample Filtering]

Figure 4:
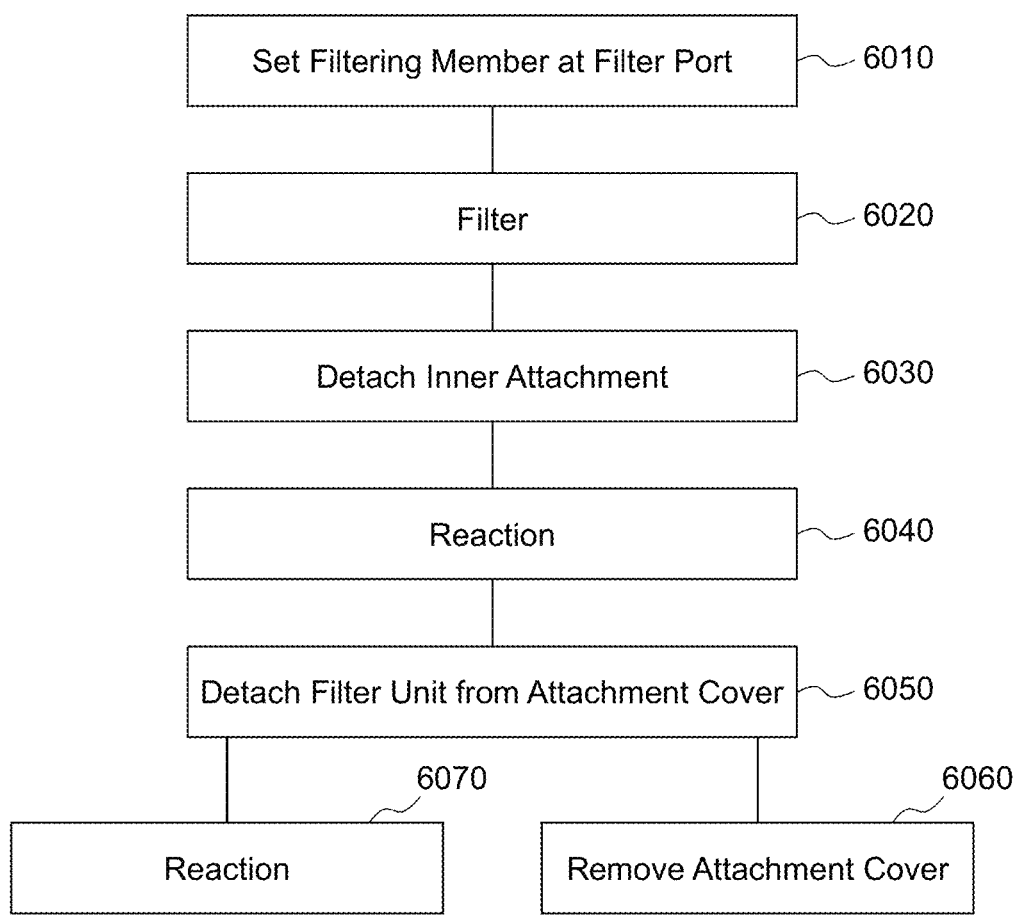
FIG. 4 illustrates a method for filtering a sample (Embodiment).

FIG. 4 illustrates the operations and process flow for filtering the sample 4030. As described previously, filtering of a sample may be manually conducted by the operator, but may also be executed by controlling a drive mechanism (not shown; for example, a gripping arm and a sample injection mechanism) and a luminescence detection unit with a control unit (i.e., computer). It should be noted that not all of the steps that are required for filtering a sample need to be implemented manually or through control by a control unit. However, description will be hereinafter made on the assumption that all steps are manually conducted by the operator.

First, the operator sets the filtering member 3700, which has been assembled from the filter unit 3010, the inner attachment 3500, and the attachment cover 3100, at the filter port 3710 (operation 6010).

Next, the operator generates a pressure difference between the upper face of the filter 3020 and the filter port 3710 to allow a sample to be filtered through the filter 3020 that is fixed on the filter unit 3010 (operation 6020).

Upon termination of the filtration, the operator detaches the inner attachment 3500 from the filter unit 3010 (operation 6030).

Next, the operator adds a reagent into the filter unit 3010 to cause a first reaction (operation 6040). As the first reaction, a reaction to remove ATP and a reaction to amplify ATP are executed, for example.

Next, the operator detaches the filter unit 3010 from the attachment cover 3500 (operation 6050). After that, the operator removes the attachment cover 3500 (operation 6060). In addition, the operator conducts a second reaction in the filter unit 3010 (operation 6070). As the second reaction, a reaction to extract ATP is executed, for example.

[Embodiment of Sample Filtering Method and ATP Bioluminescence Method]

Figure 5:
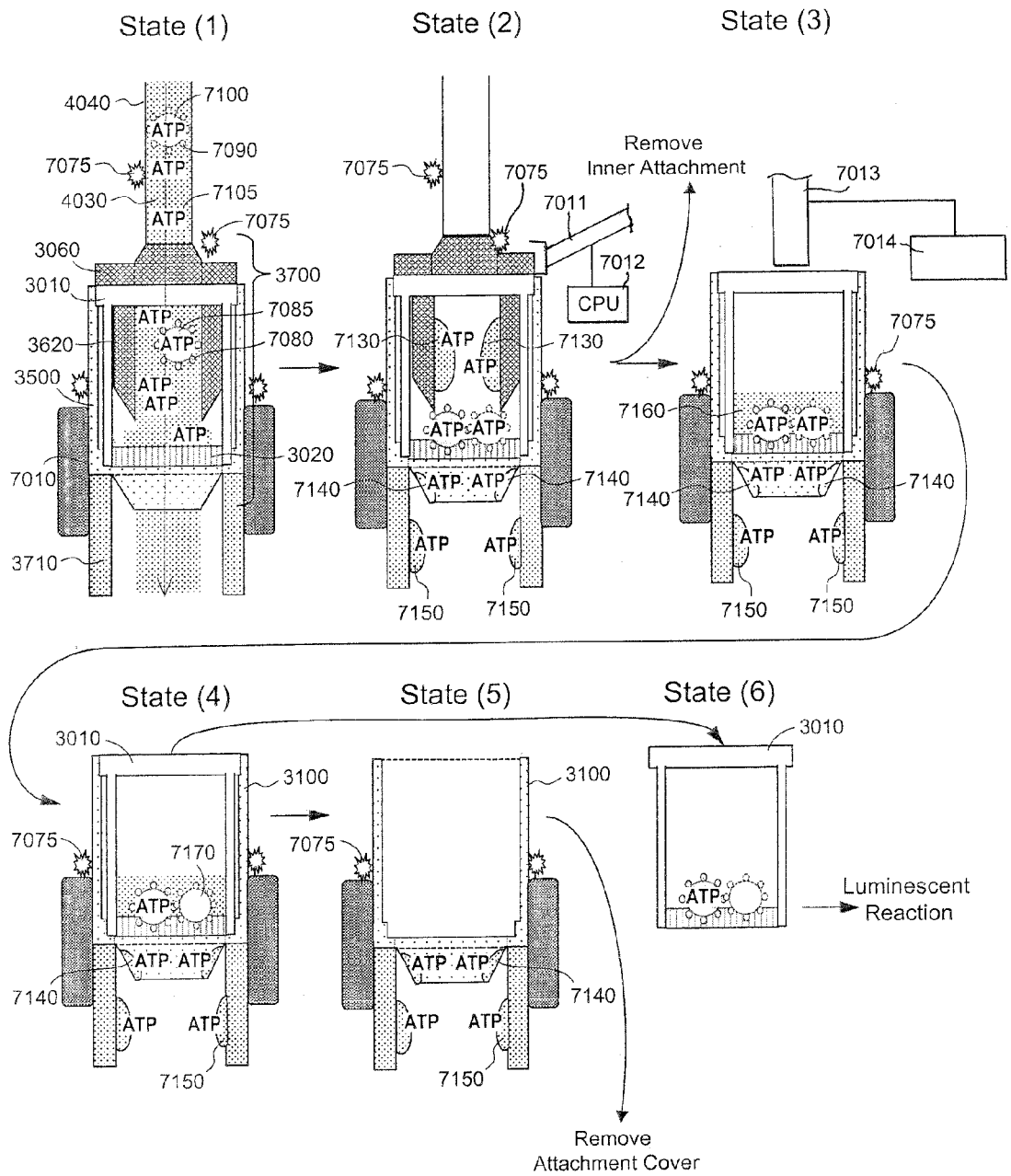
FIG. 5 illustrates a method for filtering a sample and a method for detecting ATP derived from viable bacteria.

FIG. 5 shows an embodiment of a method for filtering a sample using the filtering member 3700 in accordance with an embodiment, and the ATP bioluminescence method. In the ATP bioluminescence method, viable bacteria in a sample are measured as described below, for example. As the prerequisite operation therefor, the operator first arranges the filter port 3710, a heat block 7010, a gripping arm, and a nozzle in a sterile environment. It should be noted that the gripping arm and the nozzle may also be replaced by sterilized or disinfected tweezers, chips, and the like. Hereinafter, description will be made on the assumption that the filtering member 3700 is arranged in a sterile environment (e.g., in a clean room), and a filtering operation is executed under automatic control of a control unit (i.e., computer).

First, in a state (1), the operator sets the filtering member 3700 at the filter port 3710 with the heat block 7010 attached thereto, and connects the tube 4040 to the sample inlet 3610 of the inner attachment 3500. At this time, the operator is able to touch any place of the filtering member 3700 and the tube 4040. Therefore, the filtering member 3700 can be easily set at the filter port 3710. At this time, even when external bacterial cells or ATP contaminants 7075 stick to the surface of the filtering member 3700 or the tube 4040 from the operator or the measurement environment, there is no concern that the filter 3020 or the filter unit 3010 may become contaminated.

A region of from the tube 4040 to the sample inlet 3610 of the inner attachment 3500 includes the sample 4030 containing viable bacteria 7080 (which include ATP 7085 in the viable bacteria), dead bacteria 7090 (which include ATP 7100 remaining in the dead bacteria 7090), and ATP 7105 in the free state. The sample 4030 is introduced into the filter unit 3010 due to the pressure difference generated between the upper face of the filter 3020 and the filter port 3710, and is then filtered through the filter 3020. Filtration of the sample 4030 with the pressure difference generated is executed under control of the control unit (i.e., computer).

A state (2) shows the state in which the filtration of the sample 4030 has terminated. After termination of the filtration, an unnecessary sample 7130 containing ATP in the free state may remain on the inner wall surface of the inner attachment 3500. It should be noted that the sample 7130 containing ATP in the free state, which has stuck to the inner attachment 3500, is removed together with the contaminants 7075, inclusive of the inner attachment 3500. Removal of the inner attachment 3500 is executed by controlling the gripping arm 7011 and its drive unit with the control unit 7012.

Removing the inner attachment 3500 can prevent such unnecessary sample 7130, which has stuck to the inner wall of the sample passage 3620, from falling onto the inside of the filter unit 3010.

Although there may be cases where unnecessary filtrates 7140 and 7150 containing ATP in the free state remain on the surfaces of the attachment cover 3100 and the filter port 3701 as shown in the state (2), there is no possibility that the unnecessary sample 7130 may remain in the filter unit 3010 or on the surface of the filter 3020.

A state (3) shows the filtering member 3700 (i.e., the filter unit 3010 and the attachment cover 3100) after the inner attachment 3500 is detached. In such a state, an ATP eliminating solution 7160 is added into the filter unit 3010 through a nozzle 7013 to decompose the ATP 7100 derived from the dead bacteria 7090. The ATP eliminating solution 7160 is heated by the heat block 7010 as needed to promote reactions of the ATP eliminating solution 7160. Herein, the attachment cover 3100 is tightly attached to the side face portion of the filter 3020 of the filter unit 3010. Therefore, heat from the heat block 7010 that is arranged around the filter 3020 efficiently propagates to the ATP eliminating solution 7160 in the filter 3020. Addition of the ATP eliminating solution 7160 into the filter unit 3010 and heating of the heat block 7010 are controlled by the control unit. Addition of the ATP eliminating solution 7160 is executed through a nozzle 7013 and a nozzle drive mechanism 7014.

A state (4) represents the state after the ATP 7100 derived from the dead bacteria 7090 is eliminated (although a dead cell 7170 not containing ATP remains, such cell will not contribute to ATP bioluminescence reactions). At this time point, the filter unit 3010 and the attachment cover 3100 are separated by the gripping arm. Movement of the gripping arm is controlled by the control unit. A state (6) represents the separated filter unit 3010, and a state (5) represents the filter port 3710 at which the separated attachment cover 3100 remains.

As shown in the state (5), the filtrate 7140 that is not necessary for measurement remains as it is on the surface of the attachment cover 3100. Therefore, the possibility of re-contact between the unnecessary filtrate 7140 and the filter unit 3010 is prevented. In addition, as the unnecessary filtrate 7150 also remains as it is in the filter port 3710, the possibility of re-contact between the unnecessary filtrate 7150 and the filter unit 3010 is prevented. After that, the attachment cover 3100 is detached also from the filter port 3710. As the attachment cover 3100 that has been used is detached from the filter port 3710, there is no possibility that cross-contamination of filtrates may occur.

As shown in the state (6), the filter unit 3010 detached from the attachment cover 3100 is kept in the non-contaminated state. In such a state, a reaction to extract ATP from viable bacteria is conducted using an ATP extraction solution. Then, the ATP counts, that is, the number of viable bacteria can be accurately estimated on the basis of luminescence that occurs upon reaction between the extracted ATP and a luminous reagent containing luciferase, luciferin, or the like. The reaction to extract ATP and the detection of luminescence are executed under control of the control unit. In order to detect luminescence, an image sensor or a photosensor is used.

CONCLUSION

As described above, using the filtering member 3700 with the structure in accordance with this embodiment can execute high-sensitivity, high-precision measurement for analyzing cells in a sample. In addition, with the aforementioned filtering member 3700 and filtering method, the operator is able to easily filter a plurality of types of cells, such as viable bacteria, dead bacteria, microbes or funguses (e.g., yeast or mold), spores, non-sporulating bacteria, aerobic bacteria, anaerobic bacteria, gram-negative bacteria, and gram-positive bacteria, directly or a sample containing such cells. Accordingly, it is possible to prevent not only contamination between the operator and the sample but also cross-contamination of samples, and thus analyze cells without worrying about contamination.

In addition, using the filtering member 3700 with the structure in accordance with this embodiment and the filtering method can, even when the number of cells in a sample is small or the amount of ATP in the cells is small, further effectively measure such cells.

Further, the filtering member 3700 with the structure in accordance with this embodiment and the filtering method can be applied to a variety of sites, such as in the pharmaceutical manufacturing field, the cosmetic manufacturing field, the clinical medicine field, or the basic biochemical field. Thus, such filtering member and filtering method are effective for detection of cells and bacteria under an oligotrophic environment, for example, in managing pharmaceutical manufacturing water.

[Other Embodiments]

It should be noted that the present invention is not limited to the aforementioned embodiments, and includes a variety of variations. For example, although the aforementioned embodiments have been described in detail to clearly illustrate the present invention, the present invention need not include all of the structures described in the embodiments.

It is also possible to combine the aforementioned plurality of exemplary structures as appropriate, or add components (not shown) or replace some of components with other components (not shown).

[Comparative Examples]

Herein, filtering members with the conventional structures will be described as comparative examples. As described above, when a filtering member with the conventional structure is used for measurement with the bioluminescence method, externally generated contamination (e.g., contamination by ATP) may occur, which is problematic. Further, when a filtering member with the conventional structure is used for measurement with the bioluminescence method, internally generated contamination called cross-contamination may occur, which is also problematic. Herein, cross-contamination will be described.

When a sample is poured onto a filter or a container with a filter fixed thereon, there is a possibility that the sample may scatter around and the scattered sample may stick to a wall surface or the like around the filter and thus remain thereon. When the sample remains on the wall surface or the like around the filter, the remaining sample may become mixed with reagents while a plurality of subsequent operations are performed, which can thus cause contamination.

In particular, in the bioluminescence method in which a sample containing bacterial cells is filtered first, and then the bacterial cells on the filter are dissolved to measure light emitted from ATP extracted from the dissolved bacterial cells, it is also necessary to avoid internally generated contamination. ATP in the free state that is contained in a sample is of particular concern in the bioluminescence method. Although a sample also contains ATP of dead bacteria, such ATP can be trapped by a filter together with the dead bacteria. Meanwhile, ATP in the free state cannot be trapped by a filter and thus passes through the filter. It follows that the downstream side of the filter, that is, the filtrate contains ATP in the free state. Thus, a residue of such filtrate also becomes a source of contamination.

In the fluorescent staining method supposed in Patent Literature 1 above, the measurement targets (i.e., bacterial cells) are not contained in a filtrate in principle. That is, it is not necessary to take cross-contamination into consideration. Therefore, the microorganism collecting kit described in Patent Literature 1 cannot be directly used for measurement with the ATP luminescence measurement method. Even if such a kit is used, ATP in the free state that is contained in a filtrate will cause cross-contamination, which will make it difficult to conduct high-sensitivity, high-precision measurement.

First, the problem of contamination that is considered to occur when a filtering member with the conventional structure is used for measurement with the bioluminescence method will be described with reference to FIGS. 6-1 and 6-2.

FIG. 6A shows a filter unit 1220 obtained by attaching a filter 1210 to the bottom face of a tubular container. A state (1) represents a view in which the filter unit 1220 that stores a sample 1240 is put on a tubular filter port 1230, and the sample 1240 is filtered with a negative pressure applied. The sample 1240 contains viable bacteria 1260, dead bacteria 1270, and ATP 1275 in the free state. A state (2) represents the state after filtration. As shown in the drawing, the sample 1240 containing ATP 1280 in the free state and a filtrate containing ATP 1290 in the free state remain around the inner wall of the filter unit 1220 and the filter port 1230. Meanwhile, contaminants ATP 1295 derived from the operator or the measurement environment remain on the outer wall of the filter unit 1220.

A state (3) represents a case where an ATP extraction solution 1300 is added into the filter unit 1220 in a state in which the filter unit 1220 after termination of the filtration is mounted on a test tube 1291, so that ATP 1310 is extracted from the filter 1210. However, as shown in the state (2), if the sample 1240 remains on the inner wall of the filter unit 1220, the ATP extraction solution 1300 will act not only on the ATP 1310 extracted from the filter 1210 but also on the ATP 1280 in the free state contained in the sample 1240. That is, the ATP 1310 extracted from the filter 1210 is contaminated by the ATP 1280 in the free state contained in the sample 1240.

A state (4) represents a case where a new filter unit 1250 is put on the filter port 1230 to filter a new sample 1240. In such a case, the ATP 1290 in the free state contained in the filtrate that has remained around the filter port 1230 will regress through the filter 1210, thereby cross-contaminating the sample 1240 in the filter unit 1250.

Such contamination would also occur in the microorganism collecting kit of Patent Literature 1. The microorganism collecting kit of Patent Literature 1 includes (1) a funnel serving as a container into which a liquid sample is injected, the container incorporating a filter functioning as a pre-filter for removing foreign matter, (2) a filter plate incorporating a filter for collecting microorganisms and used by being embedded into the bottom of the funnel on the outer side, and (3) a base incorporating a filter cushion. In such a structure, the funnel incorporating the filter for removing foreign matter should be removed to access the filter plate serving as another filter. However, when only the filter plate is used, it would be difficult to retain a reagent that is necessary to extract a sufficient amount of ATP. Further, as the filter cushion incorporated in the base main body has a structure of retaining a filtrate, there is a problem in that ATP contained in the filtrate in the free state would regress to the filter, thereby contaminating other samples.

Figure 6B:
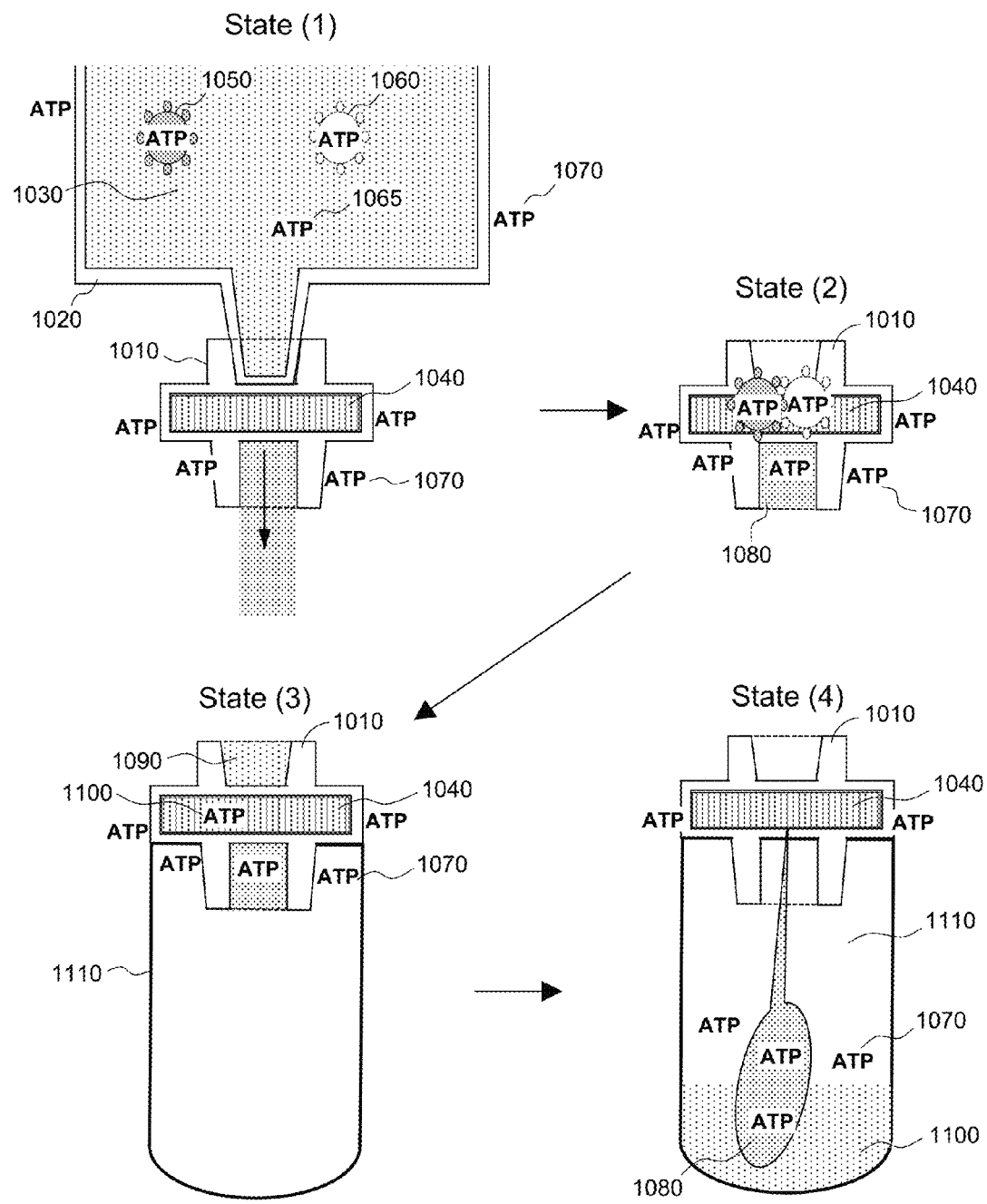
FIG. 6B illustrates a cause of contamination of a filter unit by ATP (conventional structure).

FIG. 6B shows another conventional example. A state (1) represents a view in which a syringe filter 1010 is attached to the tip end of a syringe 1020 to filter a sample 1030. It should be noted that one of the openings of the syringe filter 1010 is standardized so as to be connected to the tip end of the syringe 1020. In addition, the syringe filter 1010 has a filter 1040 fixed therein. Typically, the operator first introduces the sample 1030 containing viable bacteria 1050, dead bacteria 1060, and ATP 1065 in the free state into the syringe 1020 and attaches the syringe filter 1010 to the tip end of the syringe 1020, and then pushes a plunger (not shown) of the syringe 1020 to filter the sample 1030. The surfaces of the syringe filter 1010 and the syringe 1020 are contaminated by contaminants ATP 1070 derived from the operator.

A state (2) represents the state in which the syringe filter 1010 is detached from the syringe 1020 upon termination of the filtration. As shown in the drawing, there may be cases where a filtrate containing ATP 1080 in the free state remain in a dent of the syringe filter 1010 on the tip end side. If a filtrate remains in the syringe filter 1010, there is a possibility that when bacterial cells or substances in the bacterial cells trapped by the filter 1040 are recovered, the remaining filtrate containing ATP 1080 in the free state may contaminate the final sample.

A state (3) represents the state in which an ATP extraction solution 1090 is added into a dent of the syringe filter 1010 to dissolve the bacterial cells trapped by the filter 1040 and extract ATP 1100 in the bacterial cells. It should be noted that the drawing represents the state in which a centrifugal force is applied, or a suction force is applied, or alternatively, pressure is applied from above in a state in which the syringe filter 1010 is put on a test tube 1110, so that the extracted ATP 1100 is recovered.

A state (4) represents the state in which the target ATP 1100 is recovered in the test tube 1110. It should be noted that the state (4) represents the state in which not only the target ATP 1100 but also the contaminants ATP 1070 derived from the operator and a filtrate containing the ATP 1080 in the free state are recovered in the tube 1110. That is, both the contaminants ATP 1070 and the filtrate containing ATP 1080 in the free state contaminate the target ATP 1100.

Patent Literature 2 describes a housing in which a filter is fixed, the housing having formed therein a flow passage that is tapered from the outlet side of the filter toward the outlet of the housing. In the case of such a shape, a filtrate may remain in a section of from the outlet side of the filter to the outlet of the flow passage after termination of the filtration. In order to discard or recover the filtrate in the flow passage, a method for pushing out the filtrate by introducing air from the inlet side of the filter is used. However, there is a danger that the sterile conditions of the filter may be lost due to the introduced air or the operation therefor.

Besides, Patent Literature 3 describes a filter assembly obtained by interposing a filter between two covers, connecting a sample supply tube to one of the covers, and attaching a container to the other cover. In the assembly of Patent Literature 3, a pressure difference is generated between the upper face side of the filter and the container so as to filter a sample, and the resulting filtrate is stored in the container. It should be noted that in such a filter assembly, a flow passage for passing a filtrate is provided in the cover on the lower face side of the filter. In such a filter assembly, the filter should be collected to avoid re-contact between the filter and an unnecessary filtrate that may remain in the flow passage due to its viscosity or the like. In such a case, however, the operator should directly grasp the filter with hands for replacing the filter. Thus, it would be still difficult to avoid contamination of the filter.

Figure 7:
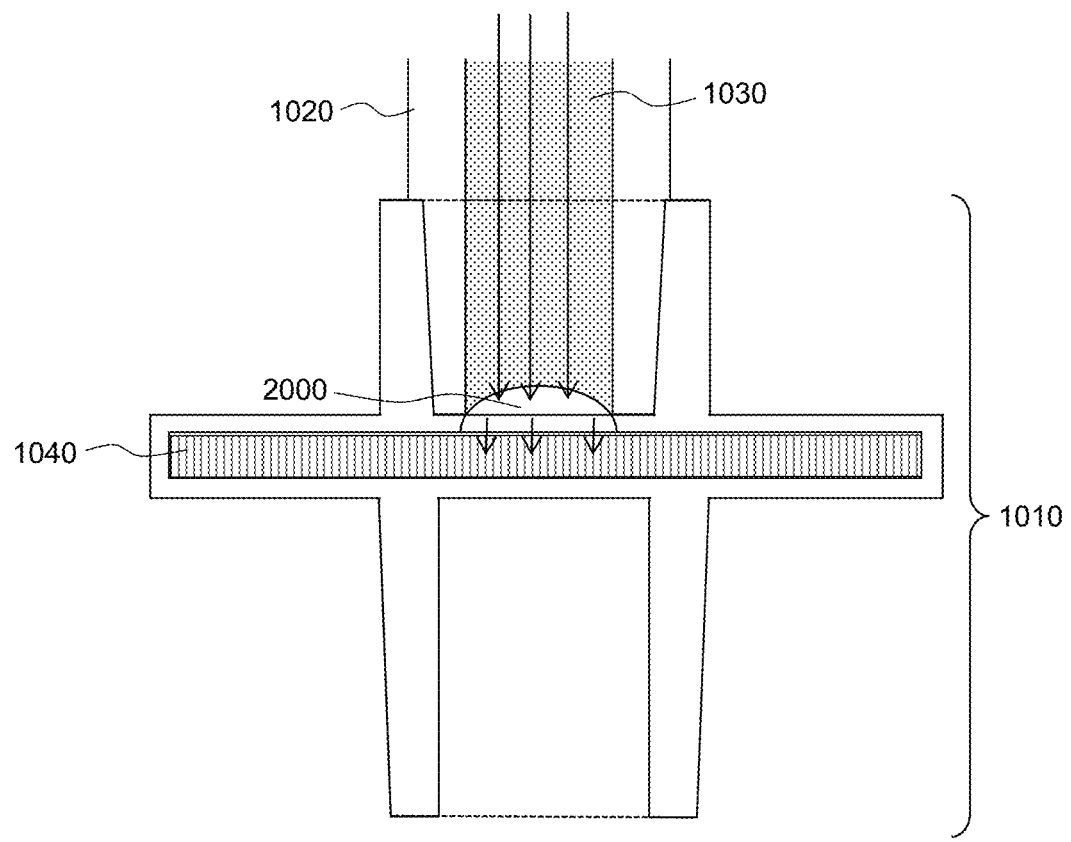
FIG. 7 illustrates a case where an air lock is generated during filtering, and filtration is thus difficult to perform (conventional structure).

Next, the problem of air locks will be described with reference to FIG. 7. FIG. 7 represents a case where a filtering member with the structure shown in FIG. 6B is used to filter a sample. FIG. 7 represents an enlarged connection portion between the syringe 1020 and the syringe filter 1010.

In this type of filtering member, there is a possibility that air bubbles may be mixed in the syringe 1020 while the sample 1030 is filtered. In such a case, air 2000 may become sandwiched between the sample 1030 and the filter 1040 that is wet by the sample 1030. As the air 2000 cannot pass through the pores of the filter 1040, the air 2000 will cover the entire surface of the filter 1040. Consequently, an air lock that would obstruct filtration of the sample 1030 is easily generated.

It should be noted that when a pressure filtration method is used, it is possible to avoid air locks by increasing the pressure applied to the sample 1030. In such a case, however, it would be necessary to separately perform pressure control and monitoring that will not break the filter 1040 or a variety of connection portions, which is problematic.

Meanwhile, when a negative pressure filtration method is used, the limit of the negative pressure applied is typically about the atmospheric pressure. Therefore, when negative pressure with a level that is greater than or equal to the atmospheric pressure is needed to pass the occluded air, the sample cannot be filtered, which is problematic. In any case, the conventional structures cannot effectively prevent air locks or would need new countermeasures, thus requiring an increase in the size and complexity of the device structure.

REFERENCE SIGNS LIST

3010 Filter unit
3020 Filter
3030 Sample inlet
3040 Housing
3100 Attachment cover
3110 Housing
3120 Filtrate passage
3210 Housing
3220 Tightly attached portion
3230 Filtrate passage
3310 Housing
3320 Filtrate passage
3410 Housing
3430 Filtrate passage 3500 Inner attachment
3505 Housing
3510 Sample inlet
3520 Sample passage
3530 Noncontact portion
3610 Sample inlet
3620 Sample passage
3700 Filtering member
3710 Filter port
4010 Viable bacteria
4020 Dead bacteria
4030 Sample
4040 Tube
4060 Droplet
4070 Temporarily residing state
4080 Space
4085 Clearance
4090 Filtrate
5020 Sample container
5030 Sample inlet cap
5050 Sample outlet cap
5040 Tilt table
7010 Heat block
7075 External bacterial cells or an ATP contaminant
7080 Viable bacteria
7085 ATP in viable bacteria
7090 Dead bacteria
7100 ATP remaining in dead bacteria
7105 ATP in the free state
7130 Unnecessary sample that contains ATP in the free state
7140 Unnecessary filtrate containing ATP in the free state
7150 Unnecessary filtrate containing ATP in the free state
7160 ATP eliminating solution
7170 Dead cell not containing ATP

The invention claimed is:

1. A filtering method for filtering a liquid with a filtering member having a (1) a filter unit, (2) an attachment cover, and (3) an inner attachment;
wherein the filter unit is mounted in the attachment cover, and the inner attachment is mounted in the filter unit;
wherein the (1) filter unit has a filter at a bottom of a container adapted for holding a liquid, the filter being adapted to filter a liquid, the (2) attachment cover has a first opening and a second opening, the filter unit being attachable to and detachable from the attachment cover via the first opening, and the attachment cover being adapted to, when the filter unit is attached to the attachment cover, allow filtration by the filter in a state in which an inner face of the attachment cover is sealingly in contact with an outer face of the filter unit, and discharge a resulting filtrate through the second opening, and the (3) inner attachment having a first opening and a second opening, the inner attachment on the first opening side being attachable to and detachable from an inside of the filter unit, and the inner attachment being adapted to, when attached to the filter unit, be in contact with the filter unit such that an outer face of the inner attachment is sealingly in contact with an inner face of the filter unit;
comprising the steps of:
1) filtering a liquid sample with the filter member;
2) detaching the inner attachment from the filter unit after step 1;
3) adding a first reaction solution into the filter unit after step 2, thereby causing at least one reaction to occur between a sample trapped by the filter and the first reaction solution;
4) detaching the attachment cover from the filter unit after step 3; and
5) adding a second reaction solution into the filter unit after step 4, causing a reaction to occur between a reactant of the trapped sample and the second reaction solution in the filter unit.

2. The filtering method according to claim 1, wherein the steps of adding the first or second reaction solutions comprise adding a reaction solution that causes at least one of the following reactions:
removal of ATP that is not derived from viable cells, removal of ATP from viable cells amplification of ATP, or extraction of ATP from the filter.

3. The filtering method according to claim 1, wherein step 3 comprises adding a first reaction solution that causes a reaction to remove ATP from cells and a reaction to amplify ATP, and step 5 comprises adding a second reaction solution that causes a reaction to extract ATP from the filter.

4. The filtering method according to claim 1, wherein the inner attachment is detached from the filter unit using a gripping arm controlled with a control unit.

5. The filtering method according to claim 1, wherein the addition of at least one of the reaction solutions is executed through a nozzle and a nozzle drive mechanism.

* * * * *